US007213593B2

(12) United States Patent
Hochrainer

(10) Patent No.: US 7,213,593 B2
(45) Date of Patent: May 8, 2007

(54) TWO-CHAMBER CARTRIDGE FOR PROPELLANT-FREE METERING AEROSOLS

(75) Inventor: Dieter Hochrainer, Bingen am Rhein (DE)

(73) Assignee: Boehringer Ingelheim KG, Ingelheim (DE)

( * ) Notice: Subject to any disclaimer, the term of this patent is extended or adjusted under 35 U.S.C. 154(b) by 25 days.

(21) Appl. No.: 11/178,690

(22) Filed: Jul. 11, 2005

(65) Prior Publication Data

US 2005/0241634 A1 Nov. 3, 2005

Related U.S. Application Data

(63) Continuation of application No. 10/638,458, filed on Aug. 11, 2003, now abandoned, which is a continuation of application No. 09/805,818, filed on Mar. 14, 2001, now abandoned, which is a continuation of application No. 09/171,471, filed on Nov. 16, 1998, now abandoned.

(30) Foreign Application Priority Data

Apr. 19, 1996 (DE) ................. 196 15 422
Apr. 18, 1997 (WO) ................ PCT/EP97/01958

(51) Int. Cl.
*A61M 11/00* (2006.01)
(52) U.S. Cl. .............. 128/200.14; 222/129; 222/82; 222/83; 206/219; 206/222
(58) Field of Classification Search ........ 128/200.14, 128/200.18, 200.19, 200.21, 200.22, 203.12, 128/203.23, 203.24; 604/86–89, 92, 415, 604/416; 366/130; 206/219, 222, 221; 222/80, 222/82, 83, 129; 220/200, 258.3, 258.4, 220/258.5
See application file for complete search history.

(56) References Cited

U.S. PATENT DOCUMENTS

| 440,316 A | 11/1890 | Long |
| 1,694,851 A | 12/1928 | Glass |
| 2,342,215 A | 2/1944 | Perelson |
| 2,362,103 A | 11/1944 | Smith |
| 2,424,801 A | 7/1947 | Crabbe et al. |
| 2,568,029 A | 9/1951 | Seemar |
| 2,629,421 A | 2/1953 | Ayres |
| 2,669,370 A | 2/1954 | Royall, Jr. |
| 2,793,776 A | 5/1957 | Lipari |
| 2,990,079 A | 6/1961 | Garvey |
| 3,172,568 A | 3/1965 | Moddema |
| 3,193,993 A | 7/1965 | Barton et al. |
| 3,198,194 A | 8/1965 | Wilburn |
| 3,255,972 A | 6/1966 | Hultgren et al. |
| 3,354,883 A | 11/1967 | Southerland |
| 3,355,238 A * | 11/1967 | Schwartzman ........ 401/41 |

(Continued)

FOREIGN PATENT DOCUMENTS

AU           230997           5/1959

(Continued)

*Primary Examiner*—Teena Mitchell
*Assistant Examiner*—Nihir Patel
(74) *Attorney, Agent, or Firm*—Michael P. Morris, Esq.; Mary-Ellen M. Devlin, Esq.

(57) ABSTRACT

A cartridge having two chambers for separate storage of active substance and solvent.

7 Claims, 4 Drawing Sheets

U.S. PATENT DOCUMENTS

| | | | |
|---|---|---|---|
| 3,425,598 A | 2/1969 | Kobermick | |
| 3,441,177 A * | 4/1969 | Treharne, Jr. | 222/82 |
| 3,625,403 A | 12/1971 | Rousselot | |
| 3,648,899 A * | 3/1972 | Lukesch et al. | 222/82 |
| 3,655,096 A * | 4/1972 | Easter | 222/82 |
| 3,674,028 A | 7/1972 | Ogle | |
| 3,842,836 A | 10/1974 | Olge | |
| 3,857,392 A | 12/1974 | Ogle | |
| 3,858,580 A | 1/1975 | Ogle | |
| 3,870,147 A | 3/1975 | Orth | |
| 3,874,380 A | 4/1975 | Baum | |
| 3,874,381 A | 4/1975 | Baum | |
| 3,878,977 A | 4/1975 | Carlisle | |
| 3,924,741 A | 12/1975 | Kachur et al. | |
| 3,946,732 A | 3/1976 | Hurscham | |
| 3,949,751 A | 4/1976 | Birch et al. | |
| 4,008,820 A | 2/1977 | Ruetz | |
| 4,019,512 A * | 4/1977 | Tenczar | 604/411 |
| 4,045,860 A | 9/1977 | Winckler | |
| 4,088,246 A * | 5/1978 | Klingaman | 222/88 |
| 4,089,432 A | 5/1978 | Crankshaw et al. | |
| 4,116,336 A | 9/1978 | Sorensen et al. | |
| 4,162,030 A | 7/1979 | Capra et al. | |
| 4,177,938 A | 12/1979 | Brina | |
| 4,187,893 A | 2/1980 | Bujan | |
| 4,195,730 A | 4/1980 | Hunt | |
| 4,201,316 A * | 5/1980 | Klingaman | 222/80 |
| 4,202,334 A | 5/1980 | Elson | |
| 4,204,606 A | 5/1980 | Micheli | |
| 4,264,018 A | 4/1981 | Warren | |
| 4,315,570 A | 2/1982 | Silver et al. | |
| 4,322,020 A | 3/1982 | Stone | |
| 4,440,316 A | 4/1984 | Christine | |
| 4,457,454 A | 7/1984 | Meshberg | |
| 4,457,455 A | 7/1984 | Meshberg | |
| 4,469,250 A | 9/1984 | Evezich | |
| 4,479,989 A | 10/1984 | Mahal | |
| 4,515,586 A | 5/1985 | Mendenhall et al. | |
| 4,516,967 A | 5/1985 | Kopfer | |
| 4,526,823 A | 7/1985 | Farrell et al. | |
| 4,559,052 A | 12/1985 | Babson | |
| 4,619,651 A | 10/1986 | Kopfer et al. | |
| 4,637,934 A | 1/1987 | White | |
| 4,638,927 A | 1/1987 | Morane | |
| 4,676,775 A * | 6/1987 | Zolnierczyk et al. | 604/28 |
| 4,727,985 A | 3/1988 | McNeirney et al. | |
| 4,732,299 A | 3/1988 | Hoyt | |
| 4,781,679 A | 11/1988 | Larkin | |
| 4,799,599 A | 1/1989 | Herrmann | |
| 4,817,830 A | 4/1989 | Yavorsky | |
| 4,821,923 A * | 4/1989 | Skorka | 222/80 |
| 4,883,641 A | 11/1989 | Wicks et al. | |
| 4,886,177 A | 12/1989 | Foster | |
| 4,979,941 A | 12/1990 | Ogle, II | |
| 4,982,875 A | 1/1991 | Pozzi et al. | |
| 5,004,123 A | 4/1991 | Stoody | |
| 5,024,087 A | 6/1991 | Nagasaki et al. | |
| 5,031,384 A | 7/1991 | Rebeyroll et al. | |
| 5,038,958 A | 8/1991 | Dreier | |
| 5,084,042 A | 1/1992 | McPhee | |
| 5,102,010 A | 4/1992 | Osgar et al. | |
| 5,105,995 A | 4/1992 | Martin | |
| 5,129,894 A | 7/1992 | Sommermeyer et al. | |
| 5,137,175 A | 8/1992 | Kowalski et al. | |
| 5,158,810 A | 10/1992 | Oishi et al. | |
| 5,176,178 A | 1/1993 | Schurter et al. | |
| 5,188,628 A | 2/1993 | Rani et al. | |
| 5,213,227 A | 5/1993 | Koyama et al. | |
| 5,242,085 A | 9/1993 | Richter et al. | |
| 5,246,142 A * | 9/1993 | DiPalma et al. | 222/129 |
| 5,273,189 A * | 12/1993 | Jouillat et al. | 222/80 |
| 5,289,818 A | 3/1994 | Citterio et al. | |
| 5,292,033 A | 3/1994 | Gueret | |
| 5,316,135 A | 5/1994 | Kneer et al. | |
| 5,316,221 A | 5/1994 | Glover et al. | |
| 5,325,977 A | 7/1994 | Haynes et al. | |
| 5,331,121 A | 7/1994 | Tsuji | |
| 5,332,113 A | 7/1994 | Kusler, III et al. | |
| 5,332,121 A | 7/1994 | Schmidt et al. | |
| 5,347,999 A | 9/1994 | Poss et al. | |
| 5,352,196 A | 10/1994 | Haber et al. | |
| 5,355,872 A | 10/1994 | Riggs et al. | |
| 5,370,272 A | 12/1994 | Gueret | |
| 5,385,251 A | 1/1995 | Dunn | |
| 5,395,365 A | 3/1995 | Weiler et al. | |
| 5,421,485 A | 6/1995 | Furuta et al. | |
| 5,455,124 A | 10/1995 | Schollenberger | |
| 5,480,067 A | 1/1996 | Sedlmeier | |
| 5,487,739 A | 1/1996 | Aebischer et al. | |
| 5,497,909 A | 3/1996 | Wirsig et al. | |
| 5,497,944 A | 3/1996 | Weston et al. | |
| 5,507,409 A | 4/1996 | Paradine | |
| 5,509,564 A | 4/1996 | Knoop | |
| 5,509,578 A | 4/1996 | Livingstone | |
| 5,511,558 A | 4/1996 | Shepard et al. | |
| 5,514,123 A | 5/1996 | Adolf et al. | |
| 5,520,972 A | 5/1996 | Ezaki et al. | |
| 5,520,975 A | 5/1996 | Inoue et al. | |
| 5,533,994 A | 7/1996 | Meyer | |
| 5,569,191 A | 10/1996 | Meyer | |
| 5,579,760 A | 12/1996 | Kohler | |
| 5,620,434 A | 4/1997 | Brony | |
| 5,642,838 A | 7/1997 | Stoody | |
| 5,657,910 A * | 8/1997 | Keyser | 222/382 |
| 5,672,321 A | 9/1997 | Daykin | |
| 5,730,328 A | 3/1998 | Maeder et al. | |
| 5,738,670 A | 4/1998 | Grippi | |
| 5,752,629 A | 5/1998 | Hardy | |
| 5,772,080 A | 6/1998 | de Pous et al. | |
| 5,782,345 A | 7/1998 | Guasch et al. | |
| 5,813,570 A | 9/1998 | Fuchs et al. | |
| 5,827,262 A | 10/1998 | Nefftel et al. | |
| 5,833,088 A | 11/1998 | Kladders et al. | |
| 5,873,491 A | 2/1999 | Garcia et al. | |
| 5,875,936 A | 3/1999 | Turbett et al. | |
| 5,878,915 A | 3/1999 | Gordon et al. | |
| 5,893,484 A | 4/1999 | Fuchs et al. | |
| 5,894,841 A | 4/1999 | Voges | |
| 5,910,138 A | 6/1999 | Sperko et al. | |
| 5,934,510 A | 8/1999 | Anderson | |
| 5,935,101 A | 8/1999 | Kato et al. | |
| 5,944,217 A | 8/1999 | Baena | |
| 5,968,619 A | 10/1999 | Carmen et al. | |
| 6,013,363 A | 1/2000 | Takahashi et al. | |
| 6,041,969 A | 3/2000 | Parise | |
| 6,062,213 A | 5/2000 | Fuisz et al. | |
| 6,062,430 A | 5/2000 | Fuchs | |
| 6,073,807 A | 6/2000 | Wilford et al. | |
| 6,109,315 A | 8/2000 | Stern | |
| 6,129,236 A | 10/2000 | Osokin et al. | |
| 6,152,296 A | 11/2000 | Shih | |
| 6,223,746 B1 | 5/2001 | Jewett et al. | |
| 6,223,933 B1 | 5/2001 | Hochrainer et al. | |
| 6,244,472 B1 | 6/2001 | Hennemann | |
| 6,280,431 B1 | 8/2001 | Domkowski et al. | |
| 6,286,700 B1 | 9/2001 | Davidson | |
| 6,364,163 B1 | 4/2002 | Mueller | |
| 6,390,332 B2 | 5/2002 | Wakayama | |
| 6,481,435 B2 * | 11/2002 | Hochrainer et al. | 128/200.14 |
| 6,598,762 B2 * | 7/2003 | McKune | 222/82 |
| 6,742,677 B2 * | 6/2004 | Petit et al. | 222/321.7 |
| 6,986,346 B2 * | 1/2006 | Hochrainer et al. | 128/200.19 |
| 7,040,311 B2 * | 5/2006 | Hochrainer et al. | 128/200.14 |
| 2001/0009151 A1 | 7/2001 | Hochrainer | |

| | | | | | | |
|---|---|---|---|---|---|---|
| 2002/0007155 A1 | | 1/2002 | Freund et al. | FR | 1159909 | 7/1958 |
| | | | | GB | 854163 | 11/1960 |
| | FOREIGN PATENT DOCUMENTS | | | IT | 449648 | 6/1949 |
| | | | | IT | 449648 | 12/1949 |
| AU | 4552085 | | 1/1986 | JP | 01-195858 | 8/1989 |
| CA | 2251828 | | 10/1997 | JP | 1195858 | 8/1989 |
| DE | 442671 | | 4/1927 | JP | 09225356 A | 9/1997 |
| DE | 28 47 929 | | 5/1980 | JP | 64-034367 | 2/1998 |
| DE | 3446697 | | 6/1986 | WO | WOX 90/06267 | 6/1990 |
| EP | 0 114 964 A1 | | 8/1984 | WO | 90/07319 | 7/1990 |
| EP | 0169501 | | 1/1986 | WO | WO 91/14468 | 10/1991 |
| EP | 0 182 094 A2 | | 5/1986 | WO | WO92/16439 | 10/1992 |
| EP | 0 217 425 | | 4/1987 | WO | WO 9323165 | 11/1993 |
| EP | 0 315 440 B1 | | 4/1989 | WO | WO943373 | 2/1994 |
| EP | 0322980 | | 7/1989 | WO | WO 95/15895 | 6/1995 |
| EP | 0 368 112 | | 5/1990 | WO | PCT US95/09384 | 2/1996 |
| EP | 0 495 330 A1 | | 7/1992 | WO | WO 96/03218 | 2/1996 |
| EP | 0532873 A1 | | 3/1993 | WO | WO 96/03344 A1 | 2/1996 |
| EP | 0577200 A1 | | 1/1994 | WO | WO9701329 | 1/1997 |
| EP | 0 622 311 | | 2/1994 | WO | WO 97/06842 | 2/1997 |
| EP | 0 585 908 A2 | | 3/1994 | WO | WO 97/12687 | 4/1997 |
| EP | 0 621 027 A1 | | 10/1994 | WO | WO97/18143 | 5/1997 |
| EP | 0635254 | | 1/1995 | WO | WO 97/26998 | 7/1997 |
| EP | 0653359 | | 5/1995 | WO | WO97/39831 | 10/1997 |
| EP | 0654419 | | 5/1995 | WO | W09827959 | 7/1998 |
| EP | 0 661 218 | | 7/1995 | WO | WO 9848943 | 11/1998 |
| EP | 0763482 | | 3/1997 | WO | WO99/43571 | 9/1999 |
| EP | 0 812 625 A2 | | 12/1997 | WO | WO 0049988 | 3/2000 |
| EP | 0629165 | | 7/1998 | WO | WO 00/27543 | 5/2000 |
| EP | 0972723 A2 | | 1/2000 | WO | WO 00/49988 | 8/2000 |
| FR | 780143 | | 4/1935 | | | |
| FR | 1.112.540 | | 3/1956 | * cited by examiner | | |
| FR | 1112540 | | 3/1956 | | | |

TWO-CHAMBER CARTRIDGE FOR PROPELLANT-FREE METERING AEROSOLS

CROSS REFERENCE TO RELATED APPLICATIONS

This application claims priority to and is a continuation of U.S. patent application Ser. No. 10/638,458, filed Aug. 11, 2003, now abandoned, which is a continuation of U.S. patent application Ser. No. 09/805,818, filed Mar. 14, 2001, now abandoned, which is a continuation of U.S. patent application Ser. No. 09/171,471, filed Nov. 16, 1998, now abandoned.

BACKGROUND OF THE INVENTION

1. Field of the Invention

The present invention relates to a two-chamber cartridge for liquids, particularly for drug formulations for use in propellant-free metering aerosols.

2. Description of Related Art

International Patent Application W091/14468 "Atomizing Device and Methods" describes a device for propellant-free administration of a metered quantity of a liquid pharmaceutical composition for use by inhalation. A further developed embodiment is described, for example, in PCT/EP96/04351. For applications of this kind it is required to package the solutions containing the active substance into containers in such a way as to include only tiny residues of air and gas. Gas bubbles would lead to uncertainty in the accurate metering of the active substance. Containers of this kind are disclosed for example in International Patent Application PCT/EP95/03183. The containers described therein are particularly suitable for those pharmaceutical compositions which can be stored for lengthy periods in the form of an aqueous or ethanolic solution. For active substances which decompose in their solutions after only a few months there have not hitherto been any suitable containers which would allow commercial use of such sensitive preparations in propellant-free metering aerosols.

BRIEF SUMMARY OF THE INVENTION

The invention now relates to a cartridge which has two chambers for separate storage of active substance and solvent. The cartridge is constructed so that, when the cartridge is inserted in a device for producing the aerosol, the chamber containing the active substance is pierced by means of a cannula, with the result that the active substance comes into contact with the solvent and is dissolved. The storage time of the pharmaceutical preparation can be extended significantly by the separate storage of active substance and solvent. The active substance may be present in the chamber as a powder, granules or in the form of a tablet. Similarly, pharmacologically acceptable excipients may be present. Generally, those galenic formulations which ensure ease of solution of the active substance in the solvent are preferred. In the case of tablets, excipients which bring about better dissolution of the tablet may be added. Similarly excipients may be added which increase the stability of the active substances. In many cases, the active substance may also be present in the chamber in dissolved form if the active substance is stable in the solvent and the solvent is miscible with the solvent in the other chamber, hereinafter also referred to as container.

BRIEF DESCRIPTION OF THE DRAWINGS

The invention is hereinafter explained in more detail with reference to some specific embodiments by way of example.

DETAILED DESCRIPTION OF THE DRAWINGS

Figure 1:
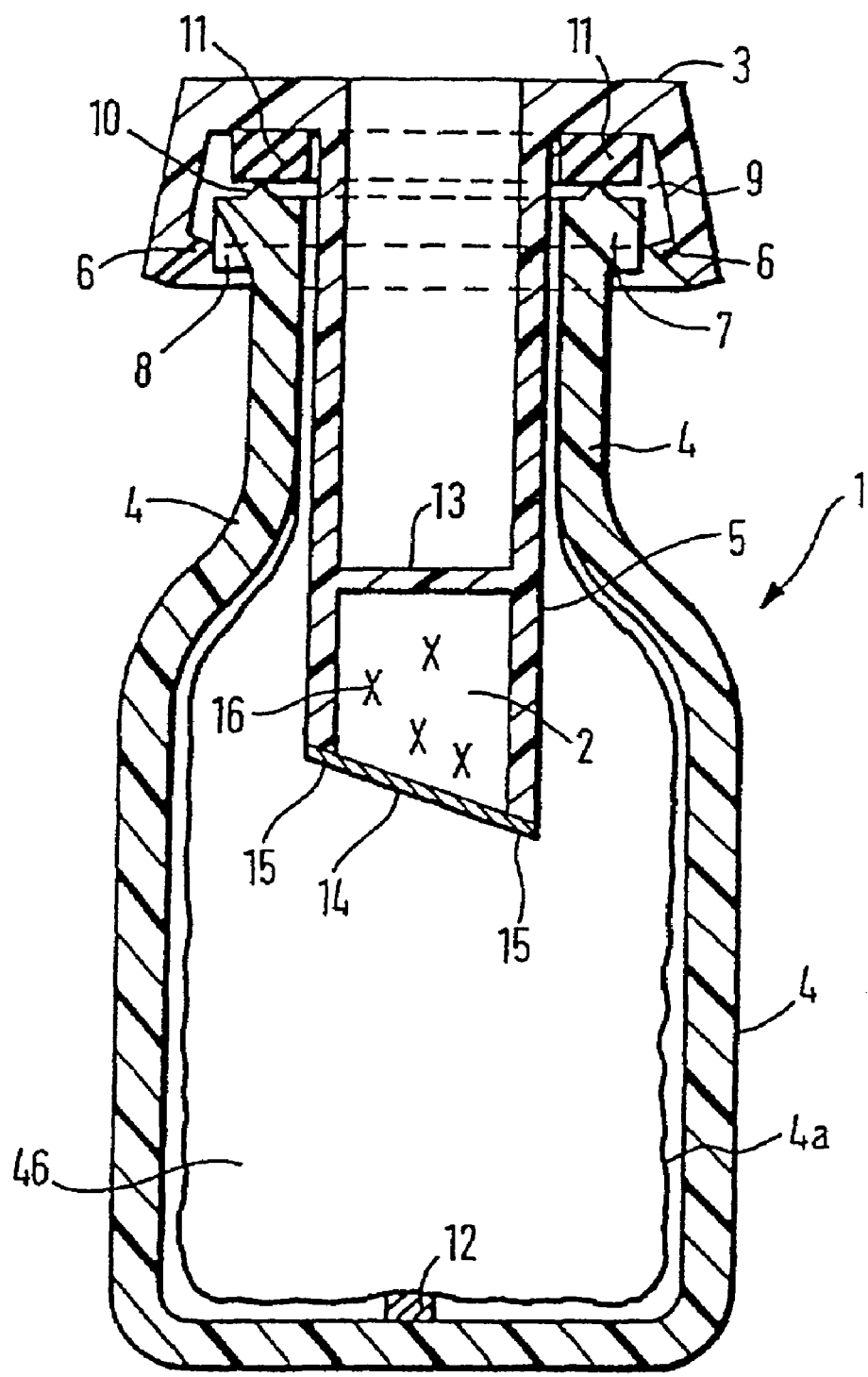
FIG. 1 shows an axial section along the longitudinal axis of the cartridge (1) in accordance with the invention with the chamber (2) for receiving the active substance, the chamber (2) being an integral part of the closure cap (3)

FIG. 1 shows the cartridge (1) in accordance with the invention consisting of a container (4) and a closure cap (3). The closure cap has a device (5)—in this case in the form of an immersed connector—through which some of the contents of the container (4) are displaced during the closure process and the container is filled with virtually no air bubbles. An internal encircling bead (6) on the lower edge of the closure cap (3) engages underneath a cylindrical ring (7) running around the outside of the neck of the container in the closed position. In the closed position the gap between the flat part of the closure cap (3) and the upper edge of the neck of the container, which may optionally have an encircling rib (10) to improve the seal, is filled by a sealing ring (11) and in this way the interior of the container (3) is sealed off. The internal diameter of the sealing ring (11) is appropriately such that it fits tightly against the connector (5). The vent opening or opening(s) (8) may also be located at other points on the outside of the cap, e.g. on the side in the cylindrical part of the cap.

In another embodiment (FIG. 2a) the closure cap (3) is closed off by a sleeve (20) made of aluminum which is crimped in position. The sleeve (20) is constructed so as to have a central opening (21) for the insertion of the cannula (22). This opening may be closed off by a septum as a protection against dust and other contaminants. This closure technique is known, for example, in injection ampoules.

In one particular embodiment the container (4) contains a collapsible internal container (4a) of flexible material. The internal container may, in a preferred embodiment, be fixed to the lower part of the container (4) by a device (12).

The chamber (2) is located in the lower part of the connector (5), the chamber being closed off to the outside by means of a partition, e.g. in the form of a septum (13), and to the interior of the container (4b) by means of a partition, e.g. in the form of a film (14). The septum (13) and film (14) are made from a material which can easily be pierced by a cannula having a pointed or rounded tip. The septum (13) is preferably made of a material which seals the interior (4b) off to the outside even when the cannula has pierced it. Usually, the partitions consist of thin plastics or aluminum foil. In one embodiment the septum (13) may have frangible points where it is connected to the side wall of the connector (5), so that when the partition is pierced it tears open at the frangible points. Preferably, the film (14) is in the form of a welded-on diffusion-tight sealing film which tears when pierced and allows the active substance to enter the interior (4b) of the container. The frangible points may also be provided in the region of the lower side wall of the connector (5) so that the lower part of the side wall of the connector is also torn away.

The position of the partition (13) may vary within wide areas of the interior of the connector (5), but it is preferably arranged in accordance with the quantity of active substance (16) so that the interior formed by the two partitions (13) and (14) contains, in addition to the powder, the least possible amount of gas (air).

Figure 2:
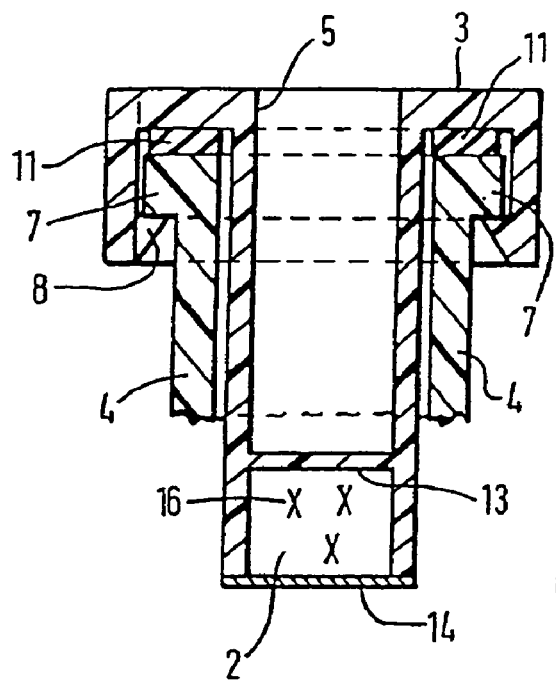
FIG. 2 shows another embodiment of the closure cap (3) with chamber (2) when the cartridge is in its closed state, the container (4) being merely indicated.
Figure 2A:
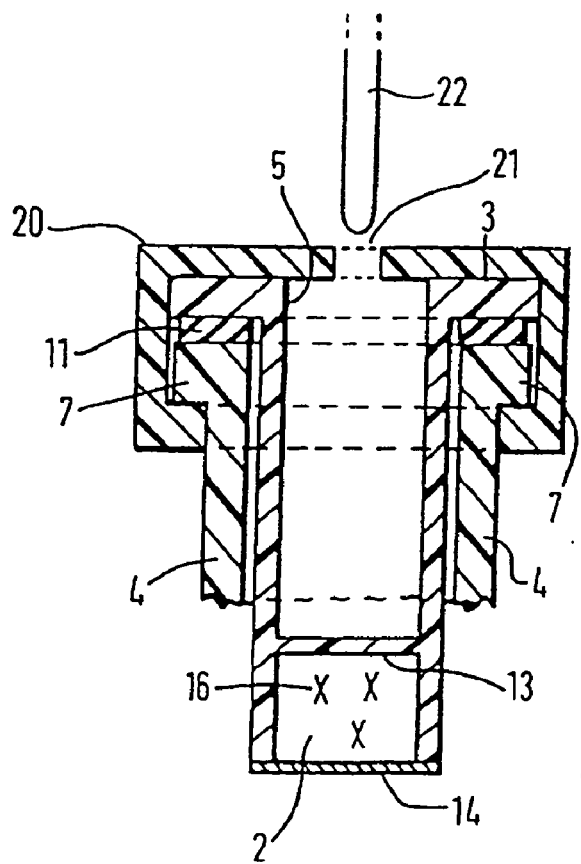

FIG. 2 also shows an axial section through the neck of a container with a closure cap (3) fitted thereon, the chamber (2) being of different configuration.

Figure 3A:
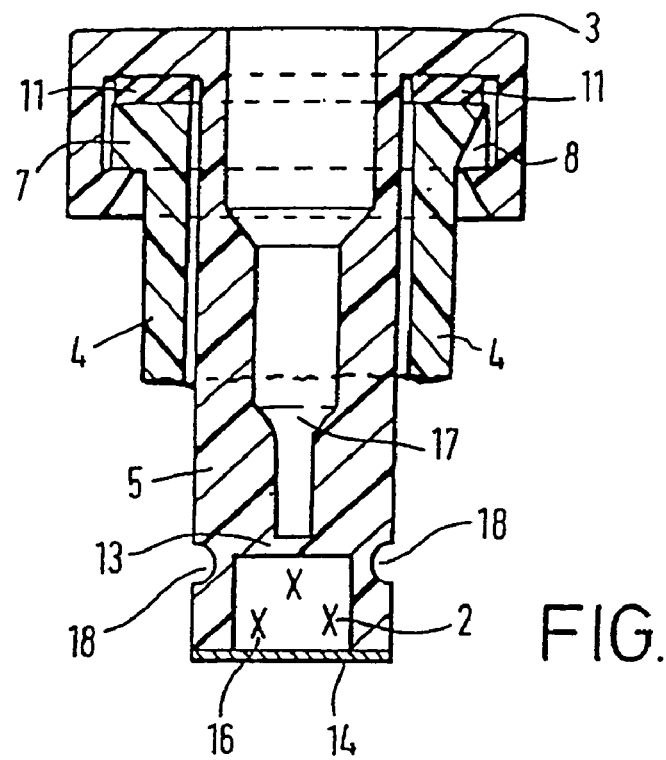
FIGS. 3a to 3c show further embodiments of the closure cap (3) in accordance with the invention with chamber (2).

FIG. 3a shows another embodiment of the closure cap according to the invention, in which the interior of the immersed connector is constructed so as to form a guide (17) for a cannula for drawing off liquid. In the present instance, the vent openings (8) are provided in the upper part of the container (4). As already described, the vent openings may alternatively be provided on the closure cap. The chamber (2) for holding the active substance is arranged separately in the lower part of the connector (5). Instead of a pierceable partition (14), frangible points (18) may be provided so that, as the partition (13) is pierced the chamber is torn away at the frangible points (18) by pressure on the partition (14). In this embodiment, the partition (14) may be constructed as the base of the connector (5).

Figure 3B:
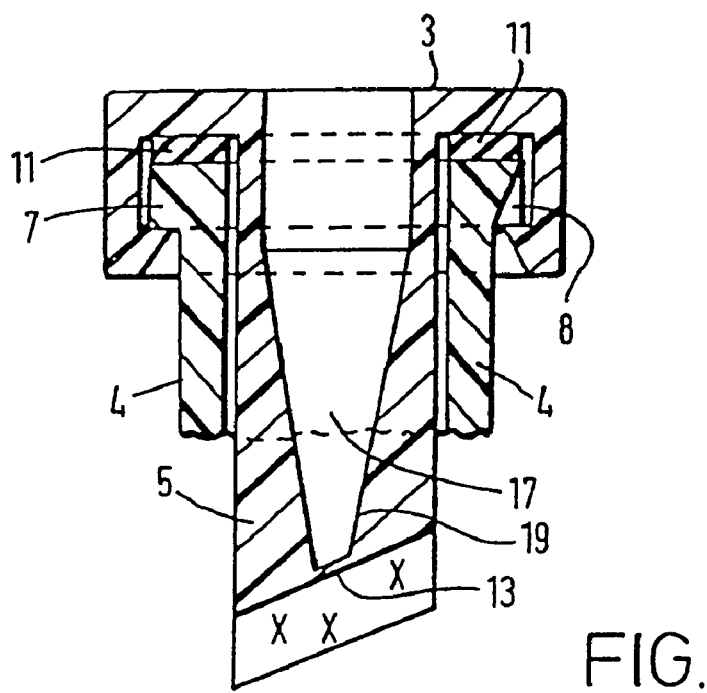
Figure 3C:
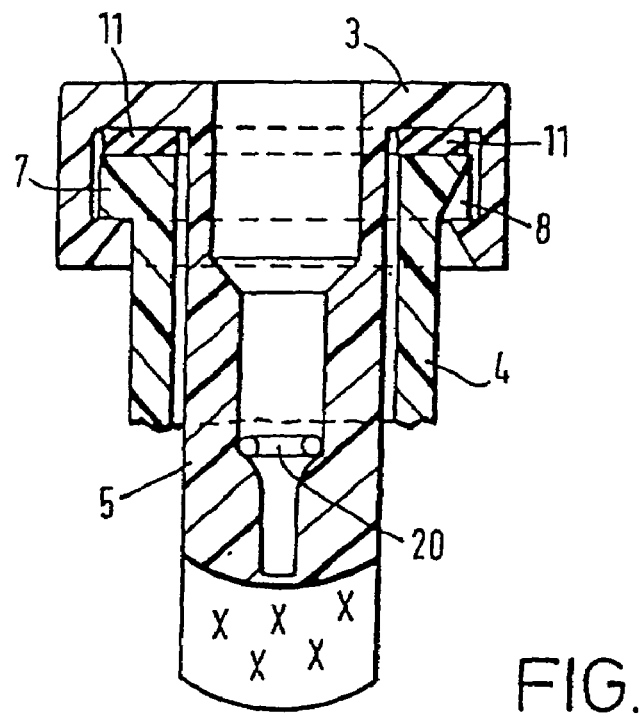

FIGS. 3b, 3c show other embodiments regarding the construction of the immersed connector (5) and the guide (17) for the cannula for withdrawing the liquid.

FIG. 3b shows an embodiment in which the guide (17) merges into a press fit (19). The press fit is designed, in terms of diameter and length, so that on the one hand the resistance for pushing the cannula through is kept to a minimum and, on the other hand, a sufficient seal is achieved between the connector and the cannula.

FIG. 3c shows an embodiment with an elastic O-ring seal (20) between the connector and the piercing cannula (not shown in the drawing). The device which prevents the O-ring from accidentally becoming detached is not shown.

As shown in FIGS. 3b and 3c, the lower end of the immersed connector with the partition (14) may appropriately be chamfered, preferably by 20° to 60° relative to the axis of the connector. This makes it easier for the partition to be pierced with a "blunt" cannula the end face of which is perpendicular to the axis of the cannula. The advantages of a "blunt" as against a "sharp pointed" cannula are the small risk of injury to the user, the reduced machining work required to produce the end face of the cannula and the reduced risk of particle abrasion on the wall of the connector as the cannula is inserted.

Figure 4:
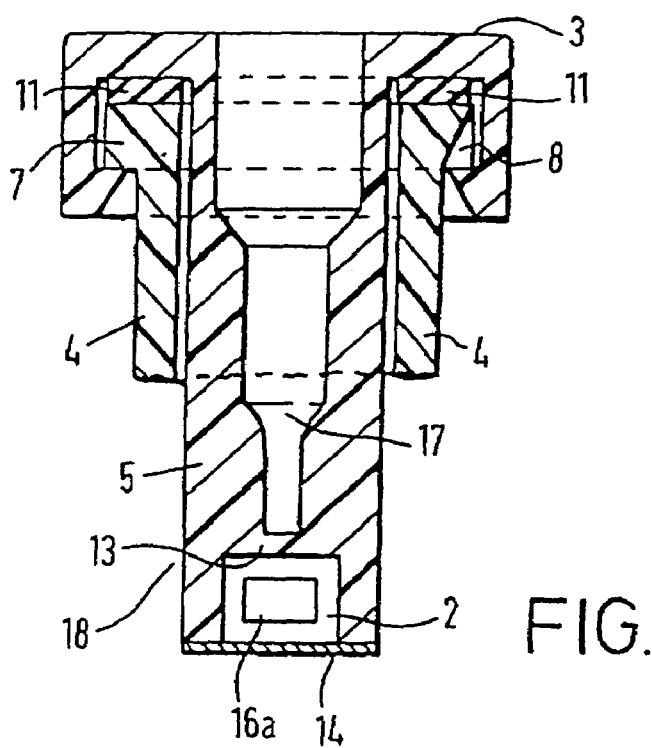
FIG. 4 shows a section along the longitudinal axis of an embodiment of the closure cap in accordance with the invention, in which the chamber (2) contains a minitablet (16a) as its supply of active substance.

As shown in FIG. 4, which corresponds largely to FIG. 3a, the chamber (2) contains the active substance in the form of a small tablet. Compared with a powdered active substance, the active substance in the form of the minitablet according to the invention is substantially easier to introduce into the chamber (2), and also a tablet has advantages when the septum (13) is pierced by a cannula and subsequently the tablet (16a) is pushed through the foil (14). On the one hand, this ensures that the relatively hard tablet does not block the cannula, and on the other hand it ensures that the full amount of active substance from the chamber enters the container (4). With the highly effective drugs commonly used in metering aerosols nowadays, a precisely metered solution of active substance is absolutely necessary for purposes of drug safety. Moreover, if the chamber (2) is filled with a tablet, the sealing surface is not contaminated with dust, as would be the case if it were filled with powder.

The tablet in accordance with the invention has a diameter of between 2 and 3 mm, preferably between 2.2 and 2.3 mm, and is between 1.8 and 3.5 mm long. The tablet in accordance with the invention has a compressive strength of between 2 and 10 $N/mm^2$. The compressive strength is measured by clamping the tablet between flat surfaces and increasing the force until the tablet breaks up. The tablets were clamped in such a way as to come into contact with the flat surfaces along two generatrices (not with the top and bottom surfaces). The compressive strength is the force divided by the cross-sectional area (diameter times length of the cylindrical tablet).

The tablets in accordance with the invention consist of the active substance and conventional tableting excipients. Preferred active substances are those which can be used in low doses, e.g. up to 100 micrograms of active substance per single dose. These include, for example, atrovent, anticholinergics, β-sympaticomimetics, e.g. formoterol. The preferred excipients are lactose (200 mesh), glucose (200 mesh) and shape separating agents.

The container in accordance with the invention has a solvent volume of 4 ml, so that 0.5% solutions of active substance can be produced with a minitablet weighing 20 mg. The solvents are preferably water or ethanol or mixtures thereof. Other physiologically acceptable solvents are also suitable.

For removing liquid from the cartridge (1) in accordance with the invention, the partitions (13 and 14) are pierced with a cannula. Preferred embodiments are those wherein the container (4) has a readily deformable inner bag (4a) and the end of the cannula is located half way up the container when the liquid is drawn off. In this case, air bubbles have the least disruptive effect. Preferably, the minitablet (16a) in accordance with the invention is used as the supply of active substance.

The container and closure cap are generally made of plastics. Since the liquid packaged therein is virtually incompressible, the system of container and closure cap must be sufficiently deformable as the liquid expands in the warm. Similarly, when the liquid is drawn off, the walls of the container must yield or collapse sufficiently. The partition generally consists of a thin plastics film. Preferably, the partition (14) consists of a thin coated aluminum which is sealed.

Containers of this kind as well as the closure cap may be produced using the suitable plastics, e.g. polyethylene or preferably polypropylene, available to those skilled in the art.

The cartridge in accordance with the invention which is for drug formulations for an inhaler should have a long shelf life. For this reason it is necessary that the solvent cannot diffuse out of the interior (4b) of the container into the chamber (2) containing the active substance before use. In addition to having a sufficiently thick-walled chamber, an aluminum coating may also be applied to the outer or inner surfaces of the chamber (2). It should be emphasized that the insertion of the cartridge with the chamber (2) in the inhaler does not require any further manual strength on the part of the patient than the insertion of a conventional cartridge.

The invention claimed is:

1. In an atomizing device for propellant-free administration of a metered quantity of a liquid pharmaceutical composition for use by inhalation, the improvement which comprises a two-chambered cartridge for separate storage of an active, pharmaceutical substance, which can be either in dry form or in liquid form, and of a liquid solvent for the active, pharmaceutical substance, both of which, when mixed, will form the liquid pharmaceutical composition to be administered by the atomizing device, which cartridge comprises:

(a) a container forming a first chamber for holding a liquid solvent within its interior, which container has a neck and around such neck is a cylindrical ring;

(b) a closure cap for the container holding the liquid solvent which closure cap has a lower edge whereby the lower edge of the closure cap engages the neck of the container by means of an internal, encircling bead on the lower edge of the closure cap and whereby the encircling bead on the lower edge of the closure cap engages underneath the cylindrical ring around the neck of the container; and (c) a non-sealing, displacing device which is provided or situated on the closure cap so as to be an integral part thereof, and so that the device will displace a portion of any liquid solvent in the container as the closure cap is pushed onto the neck of the container so that the encircling bead on the lower edge of the closure cap engages underneath the cylindrical ring around the neck of the container, and further whereby the non-sealing, displacing device has at least one second chamber within that portion of the device which would displace a portion of any liquid solvent in the container, which second chamber is suitable for storage of a pharmaceutical formulation that can be dissolved in or diluted by the liquid solvent, and whereby the device also has a cannula guide comprising an elongated tube having a vertical axis which extends from the second chamber to that area of the device situated adjacent the lower edge of the closure cap and wherein the second chamber has two openings, where one opening is from the second chamber to the guide and which is sealed by a pierceable septum, and the other opening is between the second chamber and the interior of the container which is sealed by a sealing film and the lower end of the displacing device is chamfered.

2. The atomizing device as recited in claim 1, wherein the cartridge further comprises a liquid solvent in the container and a pharmaceutical formulation within the second chamber in the non-sealing, displacing device that can be diluted or dissolved by the liquid solvent.

3. The atomizing device as recited in claim 2, wherein the chamfering of the displacing device is between about 20° to its vertical axis.

4. In an atomizing device for propellant-free administration of a metered quantity of a liquid pharmaceutical composition for use by inhalation, the improvement which comprises a two-chambered cartridge for separate storage of an active, pharmaceutical substance, which can be either in dry form or in liquid form, and of a liquid solvent for the active, pharmaceutical substance, both of which, when mixed, will form the liquid pharmaceutical composition to be administered by the atomizing device, which cartridge comprises:

(a) a container forming a first chamber for holding a liquid solvent within its interior;

(b) a closure cap; and a displacing device integral with said closure cap, the device adapted to displace a portion of at least a portion of solvent in the container as the closure cap is pushed onto the container, the displacing device further comprising at least one, second chamber therein, said chamber suitable for storage of a pharmaceutical formulation that can be dissolved in or diluted by said solvent, and further comprising a cannula guide comprising an elongated tube having a vertical axis which extends from the second chamber to that area of the displacing device situated adjacent a lower edge of the closure cap and wherein the second chamber has two pierceably sealed openings, where a first opening is disposed between the second chamber and the guide and is sealed by a pierceable septum, and the second opening is disposed between the first chamber and the second chamber.

5. The invention according to claim 4, wherein said second opening is sealed by a sealing film.

6. The invention according to claim 4, wherein a lower end of the displacing device is chamfered.

7. The invention according to claim 4, wherein said closure cap is non-removable.

* * * * *